United States Patent [19]
Kato et al.

[11] Patent Number: 5,012,670
[45] Date of Patent: May 7, 1991

[54] OXYGEN SENSOR

[75] Inventors: Nobuhide Kato, Aichi; Yasuhiko Hamada, Nagoya, both of Japan

[73] Assignee: NGK Insulators, Ltd., Aichi, Japan

[21] Appl. No.: 351,071

[22] Filed: May 12, 1989

[30] Foreign Application Priority Data

May 25, 1988 [JP] Japan .................. 63-125939

[51] Int. Cl.$^5$ .......................... G01N 27/56
[52] U.S. Cl. .................... 73/31.05; 204/428
[58] Field of Search ........ 73/23, 27; 338/34; 204/426, 428, 431, 1 T

[56] References Cited

U.S. PATENT DOCUMENTS

| 3,835,012 | 9/1974 | Hemak ................. 204/428 |
| 4,038,034 | 7/1977 | Nakajima et al. ........ 204/428 |
| 4,199,424 | 4/1980 | Teitelbaum ............. 204/428 |
| 4,401,967 | 8/1983 | Miwa et al. ............ 338/34 |
| 4,507,192 | 3/1985 | Ebizawa et al. ......... 204/428 |
| 4,597,850 | 1/1986 | Takahasi et al. ........ 204/426 |
| 4,624,770 | 11/1986 | Yamada et al. ......... 204/426 |
| 4,916,934 | 4/1990 | Nagata et al. .......... 204/428 |
| 4,929,331 | 4/1990 | Kato et al. ............ 204/426 |

FOREIGN PATENT DOCUMENTS

| 2326086 | 12/1974 | Fed. Rep. of Germany ...... 204/428 |
| 2351815 | 4/1975 | Fed. Rep. of Germany ...... 204/428 |
| 159291 | 12/1979 | Japan .................. 204/428 |
| 60-150447 | 10/1985 | Japan . |
| 1118356 | 8/1989 | Japan . |
| WO80/373 | 3/1980 | PCT Int'l Appl. .......... 204/428 |

Primary Examiner—Hezron E. Williams
Assistant Examiner—Craig Miller
Attorney, Agent, or Firm—Parkhurst, Wendel & Rossi

[57] ABSTRACT

In an oxygen sensor having a plate-shaped oxygen sensor element, a measuring electrode on the broader width surface of the plate-shaped sensor element, and a protective cover covering the plate-shape sensor element, wherein the protective cover has gas inlet holes for introducing a gas to be measured therein and guide plates for changing the direction of the flow of a gas to be measured. The gas inlet holes have different spacings compared to each other, the guide plates and the gas inlet holes have different lengths compared to each other in the axial direction of the protective cover, and/or the gas inlet holes have different opening extents compared to each other. Consequently, the oxygen sensor always can provide a homogeneous swirling flow of the gas to be measured in the protective cover as well as precise measurement of the gas and a constant λ controlling point.

3 Claims, 3 Drawing Sheets

OXYGEN SENSOR

BACKGROUND OF THE INVENTION

1. Field of the Invention

The present invention relates to an oxygen sensor, particularly to an oxygen sensor having a plate-shaped oxygen sensor element.

2. Related Art Statement

Heretofore, in order to improve precision of measurement of an oxygen sensor using a plate-shaped oxygen sensor element, applicants disclosed in Japanese Utility Model Application Laid-Open No. 60-150,447 an oxygen sensor wherein gas vent holes 5 for ventilating a gas to be measured are positioned on a protective cover 3 protecting a plate-shaped sensor element 2 such that they do not face the surface of the plate-shaped sensor element 2, as shown in the attached FIGS. 7a and 7b.

However, in the oxygen sensor of the above Japanese Utility Model Application Laid-Open No. 60-150,447, the measuring electrode 1 is arranged on a broader width surface of the plate-shaped sensor element 2, as shown in the attached FIG. 7b, so that the oxygen sensor has a drawback in that the gas to be measured impinges differently on the measuring electrode 1 depending on the attached direction of the oxygen sensor. Namely, the gas to be measured impinges in different manners on the measuring electrode 1 of the sensor element 2, depending on the direction A or B of the entrance of the gas in the protective cover 3.

If the manner of impingement of the gas to be measured on the measuring electrode 1 varies just as described above, highly precise measurements can not be performed, because the $\lambda$ controlling point of the oxygen sensor varies and the response at the low flow rate of the gas varies by the later-described reasons.

SUMMARY OF THE INVENTION

An object of the present invention is to obviate the above drawbacks and problems.

Another object of the present invention is to provide an oxygen sensor having a plate-shaped oxygen sensor element always capable of performing an optimum measurement with high precision and a constant $\lambda$ controlling point, regardless of an attached direction of the oxygen sensor.

In a first aspect of the present invention, an oxygen sensor having a plate-shaped oxygen sensor element, a measuring electrode arranged on the broader width surface of the sensor element, and a protective cover covering the plate-shaped sensor element, the protective cover, has gas inlet holes for introducing a gas to be measured therein wherein guide plates are provided on the protective cover at the gas inlet holes for changing, the direction of flow of the gas to be measured and the gas inlet holes have different spacings or distances therebetween on the circumference of the protective cover.

In a second aspect of the present invention, an oxygen sensor having a plate-shaped oxygen sensor element, a measuring electrode arranged on the broader width surface of the sensor element, and a protective cover covering the plate-shaped sensor element, the protective cover has gas inlet holes for introducing a gas to be measured therein, wherein guide plates are provided on the protective cover at the gas inlet holes for changing the direction of flow of the gas to be measured and the gas inlet holes have different extents of opening compared to each other on the circumference of the protective cover.

In a third aspect of the present invention, an oxygen sensor having a plate-shaped oxygen sensor element, a measuring electrode arranged on the broader width surface of the sensor element, and a protective cover covering the plate-shaped sensor element, the protective cover has gas inlet holes, for introducing a gas to be measured therein wherein guide plates are provided on the protective cover at the gas inlet holes for changing the direction of the flow of the gas to be measured, and the guide plates and the gas inlet holes have different lengths compared to each other in the axial direction of the protective cover on the circumference of the protective cover.

In the above described arrangements of the oxygen sensor of the present invention having the guide plates provided on the protective cover at the gas inlet holes, the gas inlet holes have different spacings therebetween such that they are unsymmetrically positioned to each other on the circumference of the protective cover and such that the gas to be measured does not impinge directly on the measuring electrode. Alternatively, the gas inlet holes have different extents of opening compared to each other such that the extents of opening are unsymmetrical on the circumference of the protective cover and the gas to be measured does not impinge directly on the measuring electrode. Alternatively, the guide plates and the gas inlet holes have different lengths compared to each other in the axial direction of the protective cover on the circumference of the protective cover such that the axial lengths of the guide plates and the gas inlet holes are unsymmetrical to each other on the circumference of the protective cover and that the gas to be measured does not impinge directly on the measuring electrode. In addition, the gas to be measured is swirled in a determined direction in the protective cover. Hence, the gas to be measured contacts with the measuring electrode always in a constant state, despite the attached direction of the oxygen sensor. Therefore, as compared with those oxygen sensors having guide plates and gas inlet holes merely of equal spacings and equal lengths, the oxygen sensor of the present invention can obtain a more favorable swirling flow and provide a more satisfactory adaptability of the oxygen sensor to the attached direction thereof.

Next, reasons will be explained why the $\lambda$ controlling point differs depending on the manners of impingement of the gas to be measured on the measuring electrode. Usually, the $\lambda$ controlling point of an oxygen sensor is shifted somewhat to the lean side from the theoretical air-fuel ratio point, as shown in the attached FIG. 6a. The shift is caused by the following phenomena. Namely, uncombusted components such as CO, hydrocarbons and the like exist in the gas to be measured such as exhaust gas from automobile engines, even if the combustion is effected in a lean (oxygen excess) atmosphere. In an ideal state, the uncombusted components react with the excess oxygen to become an equilibrating gas. In this case, the $\lambda$ controlling point coincides with the theoretical air fuel ratio point. The equilibrating reaction proceeds during the passage of the gas through the coating layer and a platinum layer of the sensor element, and reaches to the above ideal state, if it proceeds completely before reaching a three phase interface. However, in practice, the reaction does not completely proceed, and some amounts of the uncombusted components reach the three phase interface and react with $O^{--}$ in $ZrO_2$ of the sensor element to leave, for example, electrons by a reaction of $CO+O^{--} \rightarrow CO_2+2e^-$. That is, an electromotive force is generated at portions of many three phase interfaces where the uncombusted components reached, and hence an electromotive force flows even in a lean atmosphere, and the λ controlling point is apparently shifted to the lean side. Therefore, if the gas to be measured impinges strongly on the measuring electrode, the amount of uncombusted components reaching the three phase interfaces is large, so that the electromotive force becomes high (shift to the lean side is large). Conversely, if the gas to be measured impinges weakly on the measuring electrode, a vice versa phenomena occurs. Because the equilibrating reaction of the uncombusted components is promoted with an increase of the temperature, the shift to the lean side becomes small with increasing temperature of the gas to be measured (i.e., the temperature of the sensor element). Therefore, the temperature change of the sensor element depending on the manner of impingement of the gas to be measured on the measuring electrode, is also a cause of the change of the λ controlling point. As a result, in conventional oxygen sensors, the λ controlling point varies, depending on the attached direction of the oxygen sensor relative to the flow direction of the gas to be measured, as shown in the attached FIG. 6b.

BRIEF DESCRIPTION OF THE DRAWINGS

For a better understanding of the present invention, reference is made to the accompanying drawings, in which.

Figure 1A:
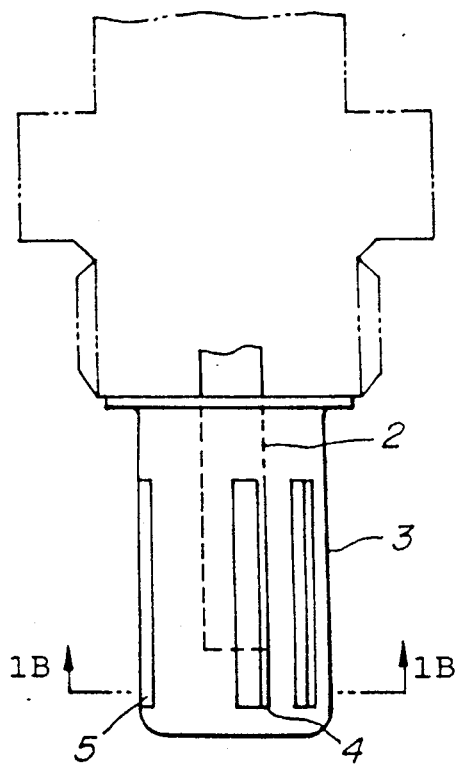
FIGS. 1a and 1b are respectively a schematic partial side view and a schematic cross sectional view along the line 1b—1b of an example of the first aspect of the oxygen sensor of the present invention.

Numberings in the drawings are as follows.
1 ... measuring electrode
2 ... plate shaped sensor element
3 ... protective cover
4 ... guide plate
5 ... gas inlet hole
l ... large extent of opening of the gas inlet hole
m ... middle extent of opening of the gas vent hole
s ... small extent of opening of the gas vent hole Throughout the different views of drawings, the same reference numerals represent the same parts or elements, unless otherwise specified.

DESCRIPTION OF PREFERRED EMBODIMENTS

Hereinafter, the present invention will be explained in more detail with reference to the accompanying drawings.

Figure 1B:
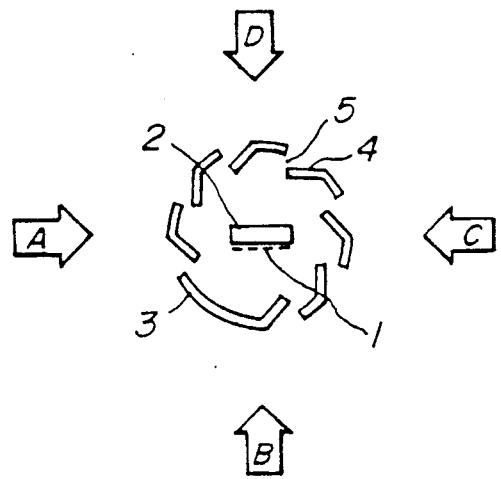

Referring to FIGS. 1a and 1b, an embodiment of the oxygen sensor of the present invention is shown, wherein a measuring electrode 1 of a known structure for detecting a gas to be measured is arranged on a broader width surface of a plate-shaped oxygen sensor element 2, the plate-shaped sensor element 2 is fixed on an oxygen sensor body (not shown) and protected, for example, by a metallic protective cover 3. A plurality of guide plates 4 are inwardly bent from the protective cover 3 with different spacing compared to each other, and a plurality of gas inlet holes 5 are formed by the guide plates 4 on the circumference of the protective cover 3 with different spacings compared to each other. The plate-shaped sensor element 2 is positioned at a height or level to correspond to a level of the gas inlet holes 5, and the protective cover 3 is oriented not to position a gas inlet hole 5 in front of the measuring electrode 1.

The oxygen sensor of the present invention of the above structure can prevent direct impingement of a gas to be measured on the measuring electrode 1, regardless of an introduced direction of the gas shown by arrows A, B, C and D, and can suppress the lean shift. Namely, a particular or biased increase of the lean shift resulting from a particular orientation of the oxygen sensor can be prevented. In this case, if a gas to be measured is introduced from the directions shown by arrows A and D, the gas swirls substantially once in the protective cover 3 prior to its impingement on the measuring electrode 1, so that a response property or responsibility of the oxygen sensor in these directions A and B is somewhat decreased. For obviating such decrease, preferably the gas inlet holes 5 facing the directions A and B have a large extent of opening or a longer length than other gas inlet holes 5 facing the directions C and D, as shown in the later described Examples.

Figure 2A:
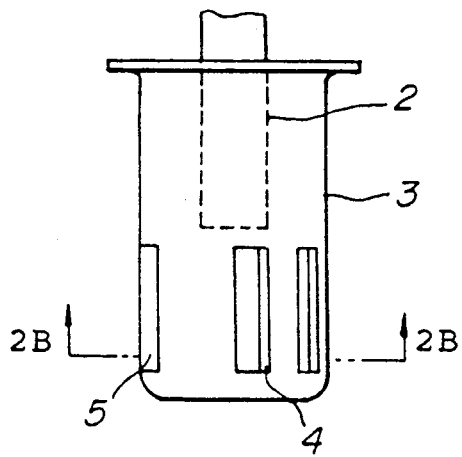
FIGS. 2a and 2b are respectively a schematic partial side view and a schematic cross sectional view along the line 2b—2b of an example of the first aspect of the present invention.
Figure 2B:
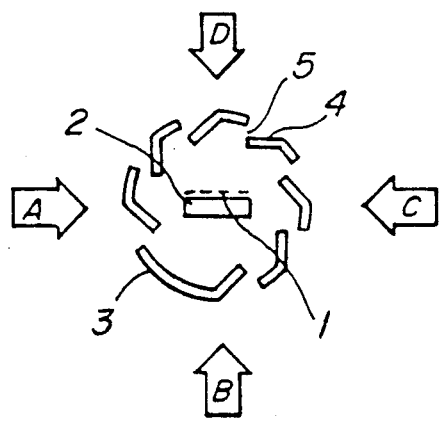

Referring to FIGS. 2a and 2b, a variation of the Example of FIGS. 1a and 1b is shown, which is different from the Example of FIGS. 1a and 1b in that the plate-shaped sensor element 2 is arranged at a level different from that of the gas inlet holes 5 so that the gas inlet holes 5 do not face directly the plate-shaped sensor element 2. Similarly, in this oxygen sensor, the lean shift can be suppressed, because a gas to be measured does not impinge directly on the sensor element 2, regardless of the introduced directions of A, B, C and D of the gas. In this case, the gas to be measured swirls in the protective cover 3, while spreading upwardly at an angle of about 30–45° from the upper ends of the gas inlet holes 5. Hence, the gas reaches the measuring electrode 1 most quickly when it is introduced in the protective cover 3 from the direction shown by an arrow B. Meanwhile, when the gas is introduced from the direction shown by an arrow D, the gas circulates about once in the protective cover 3, so that the gas reaches the measuring electrode 1 retardedly. However, the oxygen sensor has a larger number of the gas inlet holes 5 at the direction of the arrow D on the protective cover 3 than those at the direction of the arrow B, so that an amount of the gas to be introduced can be increased to compensate the retarded amount of the gas. Therefore, in the both critical cases of introduced directions B and D of the gas, the amounts of the gas to be introduced are substantially equalized, so that the λ controlling points of the oxygen sensor due to the attached direction of the oxygen sensor can be made substantially constant. Thus, the influence of the orientation of the oxygen sensor on measured results can be minimized.

Figure 3A:
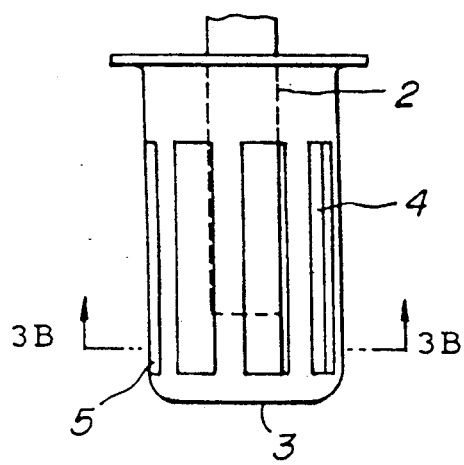
FIGS. 3a and 3b are respectively a schematic partial side view and a schematic cross sectional view along the line 3b—3b of an example of the second aspect of the present invention.
Figure 3B:
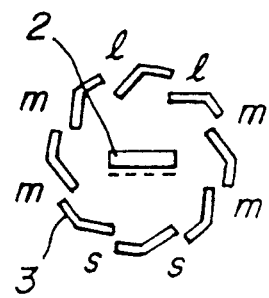
Figure 4A:
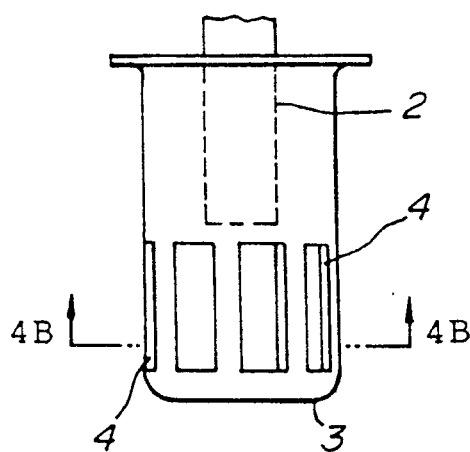
FIGS. 4a and 4b are respectively a schematic partial side view, and a schematic cross sectional view along the line 4b—4b of an example of the second aspect of the present invention.
Figure 4B:
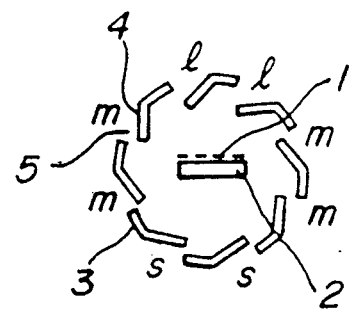

Referring to FIGS. 3a and 3b, and FIGS. 4a and 4b, embodiments of the second aspect of the present invention are shown. The embodiment in FIGS. 3a and 3b are different from the embodiment of Example of FIGS. 1a and 1b in that the extent of opening or opening extent of the gas inlet holes 5 arranged on the protective cover 3 is selected to the three extents of large, middle, and small, as shown in FIG. 3b. The embodiment in FIGS. 4a and 4b are different from the embodiment of FIGS. 1a and 1b in that the opening extent of the gas inlet holes 5 is varied similarly as of the embodiment of FIGS. 3a and 3b, and that the plate-shaped sensor element 2 is arranged at a height level different from that of the gas inlet holes 5 so that the gas inlet holes 5 do not face directly the plate-shaped sensor element 2. In either of the embodiments, a gas to be measured does not impinge directly on the measuring electrode 1 and swirls as a substantially uniform flow in the protective cover 3, regardless of the attached direction of the oxygen sensor, similarly as in the embodiment of FIGS. 1a and 1b. In addition, in the embodiment shown in FIG. 3, the gas inlet holes 5 in front of the measuring electrode 1 are made small, to assure that the gas to be measured does not impinge directly on the measuring electrode 1.

Figure 5:
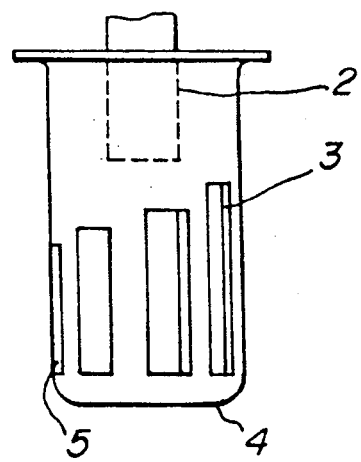
FIG. 5 is a schematic partial side view of an example of the third aspect of the present invention.
Figure 6A:
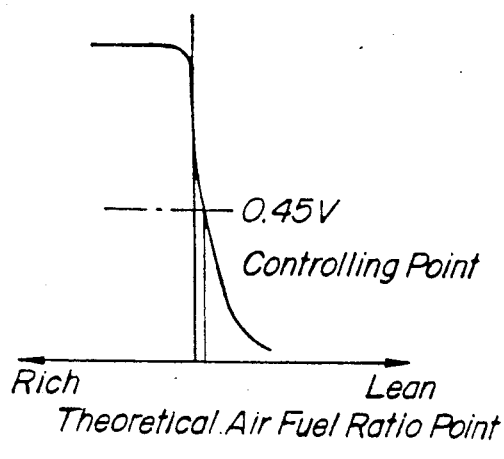
FIGS. 6a and 6b are respectively a diagram for explaining the change of the λ controlling point, depending on the manner of the impingement of the gas to be measured on the measuring electrode.
Figure 6B:
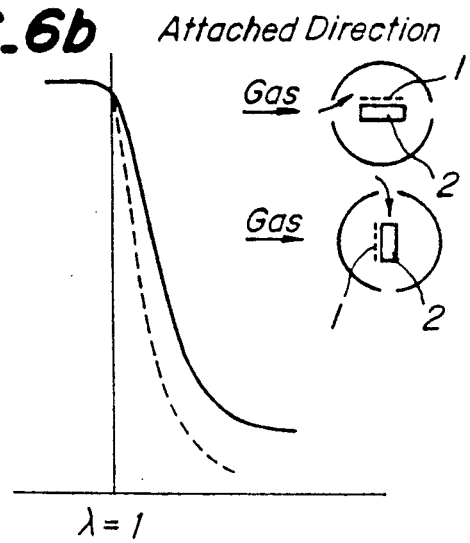
Figure 7A:
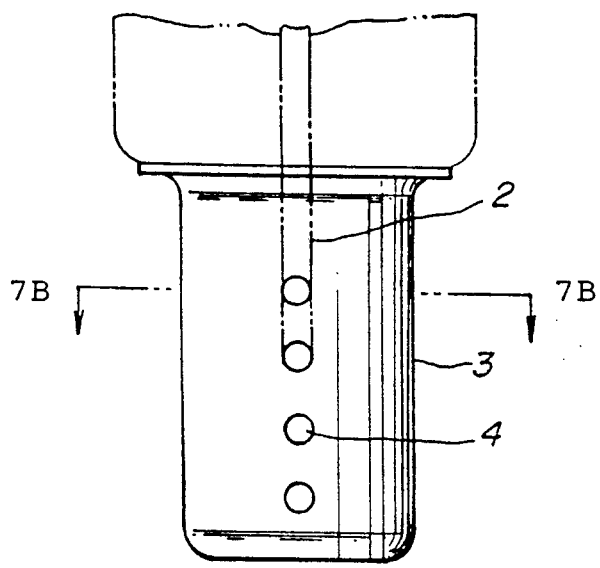
FIGS. 7a and 7b respectively a schematic partial side view and a schematic cross sectional view along the line 7b—7b of an example of a conventional oxygen sensor.
Figure 7B:
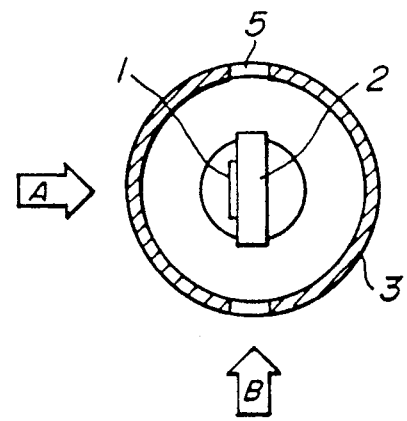

Referring to FIG. 5, an embodiment of the third aspect of the present invention is shown, which is different from the embodiment shown in FIGS. 1a and 1b in that the guide plates 4 and the gas inlet holes 5 have different lengths compared to each other in the axial direction of the protective cover 3. In this embodiment, too, a gas to be measured does not impinge directly on the measuring electrode 1 and swirls as a substantially uniform flow in the protective cover 3, regardless of the attached direction of the oxygen sensor, similarly as in the embodiment of FIGS. 1a and 1b.

The present invention can achieve satisfiable effects by a single use of any of the three aspects. Moreover, the three aspects can optionally be combined properly so as to further reduce the dependency of the swirling flow of the gas to be measured in the protective cover 3 on the attached direction of the oxygen sensor.

The downwardly projected length of the plate-shaped sensor element 2, the inner diameter of the protective cover 3, the bent angle of the guide plates 4, and the like can be selected properly so as to increase or decrease the amounts of the gas to be measured introduced at desired portions or directions of the protective cover 3.

Preferably, an opening is provided on the bottom of the protective cover 3 to exhaust the gas being measured from the opening so as to increase the amount of gas to be measured from the gas inlet holes 5 and to enhance and homogenize the swirling flow of the gas to be measured.

As seen clearly from the foregoing, the oxygen sensor of the present invention has guide plates on the protective cover at the gas inlet holes, and different spacings of the gas inlet holes, different opening extents of the gas inlet holes, and different lengths of the guide plates and the gas inlet holes in the axial direction of the protective cover, in such a fashion that they are substantially unsymmetrical on the circumference of the protective cover and a gas to be measured does not impinge directly on the measuring electrode. Consequently, the dependency of the swirling flow of the gas to be measured in the protective cover on the attached direction of the oxygen sensor can be made small, and optimum measurements of the gas to be measured with high precision can always be achieved, regardless of the attached direction of the oxygen sensor.

Although the present invention has been explained with specific examples, it is of course apparent to those skilled in the art that various changes and modifications thereof are possible without departing from the broad spirit and aspect of the present invention as defined in the appended claims.

What is claimed is:

1. An oxygen sensor comprising a plate-shaped oxygen sensor element, a measuring electrode arranged on a broader width surface of said sensor element, and a protective cover covering said sensor element, said protective cover having gas inlet holes for introducing a gas to be measured therein and comprising guide plates provided at said gas inlet holes for changing the direction of the flow of the gas to be measured, said gas inlet holes having different spacings therebetween on the circumference of said protective cover.

2. An oxygen sensor comprising a plate-shaped oxygen sensor element, a measuring electrode arranged on a broader width surface of said sensor element, and a protective cover covering said sensor element, said protective cover having a single row of gas inlet holes for introducing a gas to be measured therein and comprising guide plates provided at said gas inlet holes for changing the direction of the flow of the gas to be measured, said gas inlet holes being open to difference extents compared to each other on the circumference of said protective cover.

3. An oxygen sensor comprising a plate-shaped oxygen sensor element, a measuring electrode arranged on a broader width surface of said sensor element, and a protective cover covering said sensor element, said protective cover having gas inlet holes for introducing a gas to be measured therein and comprising guide plates provided at said gas inlet holes for changing the direction of the flow of the gas to be measured, said guide plates and said gas inlet holes having different lengths compared to each other in an axial direction of said protective cover on the circumference of said protective cover.

* * * * *